United States Patent
Zakoshansky (12) 
(10) Patent No.: US 6,943,270 B2
(45) Date of Patent: Sep. 13, 2005

(54) HIGH SELECTIVE METHOD OF PRODUCING CUMENE HYDROPEROXIDE, PHENOL AND ACETONE IN AN OXIDATION BY-PRODUCT CONVERSION PROCESS

(75) Inventor: Vladimir Mikhailovitch Zakoshansky, Long Grove, IL (US)

(73) Assignee: Illa International, LLC, Chicago, IL (US)

( * ) Notice: Subject to any disclaimer, the term of this patent is extended or adjusted under 35 U.S.C. 154(b) by 0 days.

(21) Appl. No.: 09/796,276

(22) Filed: Feb. 28, 2001

(65) Prior Publication Data

US 2002/0013502 A1 Jan. 31, 2002

Related U.S. Application Data

(60) Provisional application No. 60/243,443, filed on Oct. 26, 2000, and provisional application No. 60/186,923, filed on Mar. 3, 2000.

(51) Int. Cl.[7] ...................... C07C 45/00; C07C 409/00; C07C 37/00
(52) U.S. Cl. ................ 568/385; 568/569; 568/803
(58) Field of Search .......................... 568/385, 569, 568/803, 389, 815, 809

(56) References Cited

U.S. PATENT DOCUMENTS

| 2,735,871 | A | * | 2/1956 | Smith ........................ 568/576 |
| 2,827,493 | A | * | 3/1958 | Ermbrecht et al. ......... 568/569 |
| 3,335,070 | A | * | 8/1967 | Adams ....................... 203/37 |
| 4,358,618 | A | * | 11/1982 | Sifniades et al. |
| 5,430,200 | A | * | 7/1995 | Hood et al. |

OTHER PUBLICATIONS

Choi et al, "tetrahydron Letters", 1988, 29 (16), 1967.*

* cited by examiner

Primary Examiner—Paul A. Zucker
(74) Attorney, Agent, or Firm—Edward Etkin, Esq.

(57) ABSTRACT

A cumene process of producing phenol and acetone comprises the joint oxidation of aldehydes and dimethylbenzene alcohol by aqueous hydrogen peroxide solutions in presence of 16 wt % to 94 wt % of cumene hydroperoxide by contacting of mutually insoluble phases of the organic products from a cumene oxidation stage and hydrogen peroxide containing water with optional addition of acidic catalysts in a conversion reactor for the purpose of conversion of aldehydes into organic acids and dimethylbenzene alcohol into cumene hydroperoxide and therefore significantly simplifying the process of fractionation of organic conversion products into high quality product phenol and product acetone.

50 Claims, 2 Drawing Sheets

HIGH SELECTIVE METHOD OF PRODUCING CUMENE HYDROPEROXIDE, PHENOL AND ACETONE IN AN OXIDATION BY-PRODUCT CONVERSION PROCESS

RELATED APPLICATIONS

This application claims priority from U.S. Provisional Patent Application Ser. No. 60/186,923 entitled "High Selective Method of Producing Cumene Hydroperoxide in a Phenol and Acetone Production Process" which was filed on Mar. 3, 2000, and from U.S. Provisional Patent Application Ser. No. 60/243,443 entitled "Improved High Selective Method of Producing Cumene Hydroperoxide in a Phenol and Acetone Production Process" which was filed on Oct. 26, 2000.

FIELD OF INVENTION

The present invention is directed to petrochemical synthesis and, in particular, to a method for producing phenol and acetone from cumene via oxidation of cumene hydroperoxide and cumene oxidation by-products with hydrogen peroxide.

BACKGROUND OF THE INVENTION

Oxidation of cumene oxidation by-products (such as dimethylbenzene alcohol and aldehydes) with hydrogen peroxide to cumene hydroperoxide and organic acids, respectively, appears to achieve an advantage over conventional approaches. However, the presence of cumene hydroperoxide predetermines certain difficulties in conducting the oxidation with such a strong oxidizer as hydrogen peroxide—as a result, it is necessary to solve three absolutely different problems in order to achieve advantageous process output:

to conduct the oxidation with hydrogen peroxide in such a manner as to eliminate cumene dihydroperoxide formation from cumene hydroperoxide, while simultaneously achieving maximum aldehyde and dimethylbenzene alcohol conversion;

to conduct the oxidation by hydrogen peroxide in such a manner as to eliminate cumene hydroperoxide decomposition to phenol and acetone—representing an important safety issue; and to conduct the oxidation by hydrogen peroxide in such a manner that hydrogen peroxide remains stable and is spent preferentially for dimethylbenzene alcohol and aldehyde oxidation—representing an important economical issue.

The reaction of alcohol oxidation with hydrogen peroxide itself is a well-known chemical reaction. For example, Japanese Patent Application 55-53265 teaches the oxidation of dimethylbenzene alcohol with hydrogen peroxide in presence of aromatic hydrocarbons followed by azeotropic distillation of water formed from the hydrogen peroxide by adding benzene, which forms an azeotrope with water.

However, dimethylbenzene alcohol recovery from cumene oxidation products is almost an intractable problem. That is the reason why most researchers of various phenol processes did their best to find ways of selective conversion of dimethylbenzene alcohol from cumene oxidation stage to alpha-methylstyrene at an acidic cumene hydroperoxide cleavage stage. This has been done with some measure of success. For example, teachings of the U.S. Pat. No. 6,057,483 result in alpha-methylstyrene yield of 89.7% mole, the yield being verified in the course of said process operation at several commercial units.

In spite of high alpha-methylstyrene yield achieved in the conventional cumene process, cumene consumption per 1 ton of phenol, which characterizes total selectivity of the process, is approximately 1310–1340 kg/t. Therefore, the losses of initial cumene feed are within the range of 33–63 kg/t phenol. In addition, the problem of acetone quality resulting from presence of aldehydes almost inseparable from acetone still remains unresolved.

It would thus be desirable to provide an improved highly selective process for producing phenol and acetone in a safe and economical manner. It would also be desirable to provide an improved process that results in high quality final products. It would further be desirable to provide an improved process of greater process productivity that excludes by-products formation at the cleavage stage and the cleavage products fractionation stage.

SUMMARY OF THE INVENTION

The object of the present invention is to provide a highly selective process for producing phenol and acetone, obtaining high quality final products, increasing process productivity and excluding by-products formation at the cleavage stage and the cleavage products fractionation stage.

The substantial advantage of the inventive methodology with respect to conventional approaches involves oxidation of cumene oxidation by-products (such as dimethylbenzene alcohol and aldehydes) with hydrogen peroxide to cumene hydroperoxide and organic acids, respectively. In accordance with the present invention, the oxidation by hydrogen peroxide in a given process is not performed over individual products mentioned above but rather over the entire fraction coming from the cumene oxidation stage, i.e. technical cumene hydroperoxide. Therefore, the product containing from about 16 wt % to about 94 wt % of cumene hydroperoxide, and the very products subjected to oxidation comprising aldehydes and dimethylbenzene alcohol, are subject to oxidation by hydrogen peroxide.

As previously mentioned, the presence of cumene hydroperoxide predetermines certain difficulties in conducting the oxidation with such a strong oxidizer as hydrogen peroxide since it is necessary to solve three absolutely different problems:

to conduct the oxidation with hydrogen peroxide in such a manner as to eliminate cumene dihydroperoxide formation from cumene hydroperoxide while achieving maximum aldehyde and dimethylbenzene alcohol conversion;

to conduct the oxidation by hydrogen peroxide in such a manner as to eliminate cumene hydroperoxide decomposition to phenol and acetone, which represents a safety issue; and to conduct the oxidation by hydrogen peroxide in such a manner that hydrogen peroxide remains stable and is spent preferentially for dimethylbenzene alcohol and aldehyde oxidation, which represents an economical issue.

All aforementioned problems are solved in said improved process. The aldehyde oxidation to organic acids in the inventive process resolves the issue of acetone quality along with considerable simplification of the acetone fractionation scheme.

Advantageously, the oxidation of dimethylbenzene alcohol to cumene hydroperoxide in the inventive process eliminates the formation of such cumene hydroperoxide cleavage by-products as alpha-methylstyrene, alpha-methylstyrene dimers, o-, p-cumene phenols, and deep condensation products.

In addition, the absence of alpha-methylstyrene formation at the cumene hydroperoxide cleavage stage excludes the alpha-methylstyrene to cumene hydrogenation stage, which results in a significantly simpler and cheaper cumene hydroperoxide cleavage products fractionation stage as compared to conventional approaches.

The objectives of inventive process are achieved by treating the cumene oxidation products containing from about 16 wt % to about 94 wt % cumene hydroperoxide, dimethylbenzene alcohol, aldehydes, dicumylperoxide, and acetophenone by aqueous hydrogen peroxide solution. The reaction of aldehydes and dimethylbenzene alcohol oxidation with hydrogen peroxide is conducted at a great hydrogen peroxide molar excess with respect to dimethylbenzene alcohol and aldehydes resulting in nearly 100% conversion of the products at a rate reasonable for a commercial operation.

The process of dimethylbenzene alcohol and aldehyde conversion (hereinafter, Conversion Oxidation Process, or "COP") with hydrogen peroxide in presence of cumene hydroperoxide is carried out in a heterophase mode, i.e. due to a specially arranged contact of two mutually insoluble phases—the organic phase containing cumene hydroperoxide, dimethylbenzene alcohol, acetophenone, and aldehydes, and the aqueous phase containing hydrogen peroxide.

Experimentation with the inventive process has shown that the essential point of said heterophase process is the aqueous to organic phase ratio, which may vary from about 0.1:1 to about 10:1, respectively. A preferable phase volumetric ratio for the commercial process is from about 1:1 to about 4:1. The preferable contact temperature is about 40° C. to 75° C.

During the study of aldehyde and dimethylbenzene alcohol co-oxidation with hydrogen peroxide in presence of about 16 wt % to about 94 wt % cumene hydroperoxide, it was discovered that the hydrogen peroxide content in the aqueous phase may vary from about 1 wt % to about 70 wt %, however, the preferable hydrogen peroxide concentration to achieve the required high degree of aldehyde conversion to acids and dimethylbenzene conversion to cumene hydroperoxide ranges from about 20 wt % to about 50 wt %.

One distinguishing feature of the COP over conventional approaches is recycling the aqueous phase containing hydrogen peroxide back to a dimethylbenzene alcohol to CHP conversion reactor. The additional amount of water formed during reaction is removed from the process in the fractionation column while recycling back concentrated hydrogen peroxide from a fractionation column and ensuring that the hydrogen peroxide solution composition maintains a substantial constant concentration in the conversion reactor. Another distinguishing feature of the COP is that it is carried out in presence of a high amount of cumene hydroperoxide of about 16 wt % to about 94 wt %.

There are no analogues to the inventive process among previously known approaches in that in the inventive process the reaction of aldehyde and dimethylbenzene alcohol oxidation may be conducted with hydrogen peroxide without adding acidic catalysts into the reactor. Without addition of acidic catalysts to the reactor, the process is carried out at a higher temperature from 60° C. to 75° C.

As the results of experimentation with the inventive process have shown, such organic acids as formic, acetic, propionic or mixtures thereof, as well as chlorine substituted aforementioned acids can be used to increase the rate of the reaction of aldehyde and dimethylbenzene alcohol oxidation with hydrogen peroxide. Usage of organic acids for the reaction of aldehyde and dimethylbenzene alcohol co-oxidation either in absence or in presence of cumene hydroperoxide has never been described or disclosed in descriptions of conventional previously known techniques or processes.

The range of organic acids concentration dependent on their strength in this process is from about 0.1 wt % to about 20 wt %. An important advantage of using organic acids in this process is that the acids, while accelerating the reaction of aldehyde and dimethylbenzene alcohol oxidation with hydrogen peroxide, do not cause its decomposition in the products cumene hydroperoxide to phenol and acetone.

Usage of a strong acid catalyst, such as sulfuric acid, for conducting the reaction of dimethylbenzene alcohol oxidation with hydrogen peroxide in an inert solvent medium is practically possible and is known from Japanese Patent Application 55-53265. However, the aldehyde and dimethylbenzene co-oxidation with hydrogen peroxide in presence of about 16 wt % to about 94 wt % cumene hydroperoxide and simultaneous presence of such a strong mineral acid as sulfuric acid has not been previously taught and is extremely dangerous. A well-known fact is that the acidic cumene hydroperoxide cleavage is characterized by a significant heat generation of about 380 Kcal/kg cumene hydroperoxide that is equivalent to an adiabatic temperature increase by about 700° C., which actually results in a heat explosion. That is why one key objective for possible use of strong mineral acids for oxidizing aldehydes and dimethylbenzene alcohol with hydrogen peroxide in presence of cumene hydroperoxide in the inventive process was to discover process conditions that would prevent the reaction of acidic cumene hydroperoxide cleavage.

Advantageously, the inventive process is performed under conditions that allow using strong mineral acids for oxidizing aldehydes and dimethylbenzene alcohol with hydrogen peroxide in presence of 16 wt % to 94 wt % cumene hydroperoxide without any decomposition of said cumene hydroperoxide to phenol and acetone. In the inventive process, this result was achieved by creation of a heterophase system where the acidic catalysts are nearly completely contained in aqueous phase where the cumene hydroperoxide solubility is very low, and the reaction of aldehyde and dimethylbenzene alcohol oxidation occurs either in the organic phase or at the aqueous and organic interface. The volumetric ratio of aqueous to organic phase should be kept not less than about 1:1, and the mineral acids concentration of the aqueous phase depending on their strength is from about 0.5 wt % to about 0.005 wt %. Oxidation of aldehydes with hydrogen peroxide is of great practical importance for a commercial phenol/acetone production process from the standpoint of acetone product quality. For example, even few ppm of formaldehyde present in acetone decrease the KT value of the acetone product by several hours, which characterizes the acetone oxidation stability, and thereby deteriorates the consumer properties of the acetone product.

A similar effect on KT value is observed for acetaldehyde and propionic aldehyde. It is almost impossible to separate the aforementioned aldehydes from acetone by fractionation methods, therefore the industry uses expensive, labor-intensive, and power-intensive processes of alkaline acetone treatment. Under alkali, aldehydes are subjected to aldol condensation. However, even at significant alkali excess, aldehydes cannot be completely condensed to aldols and thereby removed from acetone. In addition, the alkaline acetone treatment causes the formation of diacetone alcohol, which deteriorates the acetone quality.

In the inventive process, the cumene oxidation by-products $C_1$–$C_3$ aldehydes are oxidized to organic acids by hydrogen peroxide. This completely resolves the acetone quality problem. The practical importance of dimethylbenzene alcohol oxidation to cumene hydroperoxide with hydrogen peroxide is well understood. Instead of dimethylbenzene alcohol by-product, this reaction forms desired product such as cumene hydroperoxide used further to produce phenol and acetone. Therefore, both the overall selectivity and the productivity of the entire cumene process for producing phenol and acetone are increased in proportion to the amount of dimethylbenzene alcohol formed at the first stage of said process, which is the stage of cumene oxidation with air oxygen.

BRIEF DESCRIPTION OF THE DRAWINGS

In the drawings, wherein like reference characters denote corresponding or similar elements throughout the various figures.

DESCRIPTION OF THE PREFERRED EMBODIMENT

In summary, the main novelty of the chemical reactions and technological implementation of the improved cumene process of producing CHP, phenol and acetone of the present invention may be characterized by the following: causing a joint oxidation of aldehydes and dimethylbenzene alcohol by an aqueous hydrogen peroxide solution in presence of 16 wt % to 94 wt % of cumene hydroperoxide by contacting of mutually insoluble phases of the organic products from the cumene oxidation stage and hydrogen peroxide containing water with or without addition of acidic catalysts in a conversion reactor for the purpose of conversion of aldehydes into organic acids and dimethylbenzene alcohol into cumene hydroperoxide.

Treated with hydrogen peroxide, cumene oxidation products are separated from said hydrogen peroxide and sent to subsequent stages of acidic cumene hydroperoxide cleavage, neutralization, and cumene hydroperoxide cleavage products fractionation according to the simplified scheme of the present invention as compared to the more complex conventional cumene process.

The cumene oxidation products treatment by hydrogen peroxide is a heterophase process wherein the aqueous phase contains about 1 wt % to about 70 wt % of hydrogen peroxide, whereas the organic phase contains about 16 wt % to about 94 wt % of cumene hydroperoxide, dimethylbenzene alcohol, $C_1$–$C_3$ aliphatic aldehydes, benzoic aldehyde, and dicumyl peroxide. The two different phases are contacted by a mixing devise in the conversion reactor at a temperature range from about 40° C. to about 75° C.

Preferably, a combination hydrogen peroxide stabilizing agent and acidic catalyst (such as 0.1 wt % to 0.5 wt % aqueous phosphoric acid) is added to the conversion reactor to stabilize the hydrogen peroxide and to accelerate the conversion reaction. Optionally, organic acids such as formic acid, acetic acid, chloracetic acids, propionic acid, or mixtures thereof, as well as strong mineral acids such as sulfuric, chlorhydric, and perchloric acids, may be added to the conversion reactor to promote the aldehyde and dimethylbenzene alcohol oxidation reactions. The aqueous to organic phase volumetric ratio in the reactor is maintained in the range of about 0.1:1 to about 10:1, respectively; (and preferably in the range of about 1:1 to about 1:6, respectively).

The process is conducted in the conversion reactor in a manner to achieve substantially complete oxidation of the aldehydes and dimethylbenzene alcohol utilizing hydrogen peroxide, and almost completely exclude acidic cumene hydroperoxide cleavage. Due to aldehydes oxidation to corresponding organic acids that, unlike aldehydes, are easily separated from desired products, the acetone from the inventive cumene hydroperoxide cleavage stage is of very high quality and is specifically characterized by high stability to oxidation.

Dimethylbenzene alcohol oxidation to cumene hydroperoxide eliminates any unselective dimethylbenzene alcohol conversions into alpha methylstyrene dimers and complex phenols at the cumene hydroperoxide cleavage stage, and also eliminates any unselective dimethylbenzene alcohol and alpha methylstyrene conversions at the fractionation stage. These qualities result in the inventive cumene process being significantly more selective than previously known processes. Because of almost negligible presence of dimethylbenzene alcohol conversion by-products in the cumene hydroperoxide cleavage products, the fractionation of these products becomes significantly easier comparable to conventional cumene processes. Furthermore, due to the stage of cumene oxidation products treatment by hydrogen peroxide incorporated into the inventive process, experimentally, the process shows a cumene usage value of 1285 kg/t phenol, which is very close to the theoretically achievable overall cumene usage of 1277 kg/t.

Figure 1:
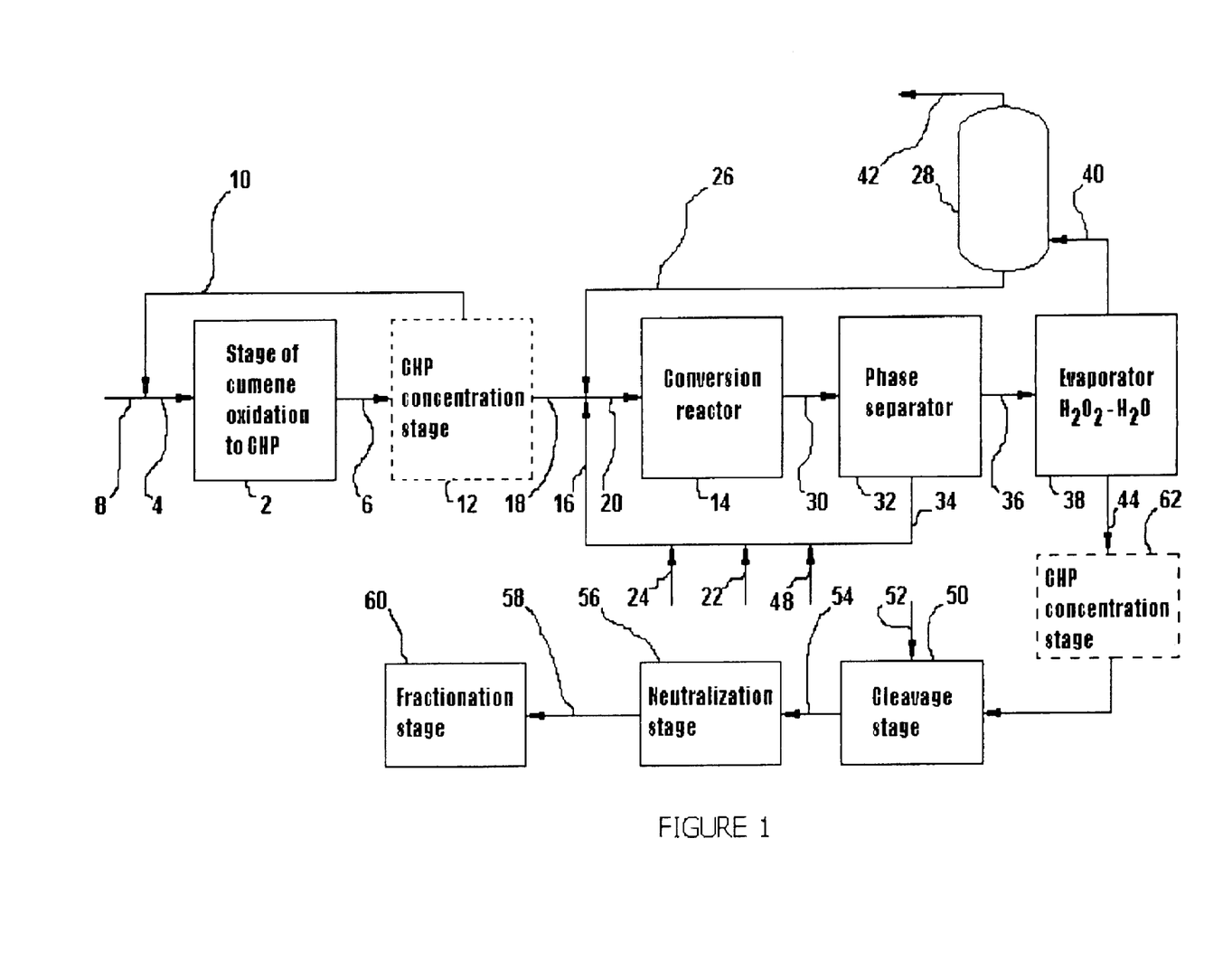
FIG. 1 schematically represents the inventive process including the stage of hydrogen peroxide treatment of the cumene oxidation products containing cumene hydroperoxide, dimethylbenzene alcohol, and aldehydes.

Referring now to FIG. 1, the inventive process for producing CHP, phenol and acetone is shown. A stage 2 of cumene oxidation with air oxygen is running in a conventional manner to produce, from a stream 4, oxidate 6 containing 16 wt % to 45 wt % of cumene hydroperoxide as the main reaction product and oxidation by-products such as dimethylbenzene alcohol, acetophenone, aliphatic $C_1$–$C_3$ aldehydes, and benzoic aldehyde. Stream 4 is at least a mixture of fresh cumene 8 and recycle cumene 10 from an optional cumene hydroperoxide concentration stage 12. The optional cumene hydroperoxide concentration stage 12 is advantageous because higher CHP concentration in the cumene oxidation products provides better process selectivity. However, if the stage 12 is omitted from the process after stage 2, another CHP concentration stage will be necessary later in the process.

After stage 2 (and after stage 12 if it is utilized) the cumene oxidation products are fed to a conversion reactor 14 for treating the cumene oxidation products by an aqueous hydrogen peroxide solution. The effluent from stage 2 (or optional stage 12), i.e. technical cumene hydroperoxide, is fed to the conversion reactor 14 along with an aqueous hydrogen peroxide solution 16 containing from about 1 wt % to about 70 wt % (and preferably from about 20 wt % to about 50 wt %) of hydrogen peroxide. It should be noted that the approximate desired concentration of the hydrogen peroxide solution 16 should be selected from the preferable 20 to 50 wt % range during process design and maintained substantially at the selected value.

Stream 6 from stage 2 contains about 16 wt % to about 45 wt % of the main product, i.e. cumene hydroperoxide, and also cumene and cumene oxidation by-products such as dimethylbenzene alcohol, acetophenone, aldehydes, and dicumyl peroxide. If the optional stage 12 is utilized, stream 18 may contain about 60 wt % to about 94 wt % of the main product (i.e., cumene hydroperoxide), cumene and also cumene oxidation by-products such as dimethylbenzene alcohol, acetophenone, aldehydes, and dicumyl peroxide.

The content of the cumene oxidation by-products comprising dimethylbenzene alcohol, aldehydes, dicumyl peroxide, and acetophenone, depends on the selectivity achieved at stages 2 and/or 12, however their total concentration does not exceed about 9 wt % in a stream 20 fed to the conversion reactor 14. Stream 16 of aqueous hydrogen peroxide solution containing a stable concentration value selected preferably from about 20 wt % to about 50 wt % of hydrogen peroxide is also added to the conversion reactor 14 via stream 20.

Stream 6 from stage 2 (or stream 18 from stage 12, if stage 12 is utilized) and the aqueous hydrogen peroxide solution 16 are introduced to the conversion reactor 14 where the reaction of dimethylbenzene alcohol and aldehyde conversion occurs under intensive mixing of mutually insoluble aqueous and organic phases, which qualifies the process as a heterophase type process.

The reactions that occur in the conversion reactor 14 may be described by the following chemical equations:

[1]

where $R_1$ represents $C_1$-, $C_2$-, alkyl-or aryl-radicals.

[2]

Dimethylbenzene alcohol $C_6H_5$—$C(CH_3)_2$—O—OH + $H_2O$

Cumene hydroperoxide

Experimentation with the inventive process proved that reactions [1] and [2] occur in the conversion reactor 14 either with or without presence of acidic catalyst, or a mixture thereof, to the conversion reactor 14. Therefore, a commercial conversion oxidation process may be carried out either with or without the specific addition of acidic catalysts to the conversion reactor 14. Of course addition of an acidic catalyst will accelerate the catalysts accelerate the process of dimethylbenzene alcohol and aldehyde conversion in the conversion reactor 14.

An optional catalyst stream 22, fed into stream 16, can be selected from a variety of organic acids such as formic, acetic, propionic, and benzoic or mixtures thereof, chlorine substituted above mentioned acids such as monochloracetic, dichloracetic, and trichloracetic, and mineral acids such as chlorhydric, sulfuric, and orthophosphoric. Other types of acid catalysts may be one of or a mixture of several of the following acids: fluorine, chlorine substituted acids of aliphatic range, mineral acids including at least $H_3PO_4$, $H_2SO_4$, HCl, $HClO_4$, $H_2SO_3$, $SO_2$, heterogeneous acidic catalysts including sulfanic ion exchange resins, naphiones, and acidic zeolites.

The volumetric ratio of the aqueous phase containing hydrogen peroxide to the organic phase containing cumene hydroperoxide, dimethylbenzene alcohol, and aldehydes is maintained in the conversion reactor 14 in the preferable range of about 1:1 to about 6:1, respectively. However, the inventive process will still function well at a volumetric ratio of 0.1:1 to about 10:1. The concentration of the hydrogen peroxide in the aqueous phase is maintained in the conversion reactor 14 at a predefined substantially stable value selected from a preferable range of about 20 wt % to about 50 wt %. However, the inventive process will still function even if the predefined stable value is selected from a range between about 1 wt % to about 70 wt %.

In order to maintain the insolubility of the aqueous and organic phases it is important to keep the hydrogen peroxide concentration at a relatively stable selected level. This may be accomplished via at least two mutually compatible approaches. In one approach, additional aqueous hydrogen peroxide solution 24 and recycle 26 from a fractionation column 28 bottom are added to the conversion reactor 14 in regulated quantities. In another approach a stabilizing agent 48 is added to a stream 34 and delivered to the reactor 14. Alternately, the particular acid used in the catalyst stream 22 may be selected so as to have a stabilizing effect on hydrogen peroxide as well as a catalytic influence on the conversion process. In this case, there is no need to provide a separate stabilizing agent 48. However, the additional stabilizing agent 48 can still be added as a matter of design choice to improve hydrogen peroxide stability. Preferably, aqueous phosphoric acid may be delivered via catalyst stream 22 to serve the dual roles of the hydrogen peroxide stabilizing agent and catalyst. For optimal performance the concentration of the aqueous phosphoric acid in the hydrogen peroxide aqueous phase should be maintained at about 0.1 wt % to about 0.5 wt %.

The temperature in the conversion reactor 14 should be maintained from about 40° C. to about 75° C. The temperature value is preferably selected so as to provide the required conversion of aldehydes and dimethylbenzene alcohol in both variants of conducting the conversion oxidation process—i.e. with or without presence of the acidic catalyst in the conversion reactor 14. If the optional catalyst stream 22 is utilized to deliver mineral acid(s) as a catalyst, then, preferably the mineral acids concentration of the aqueous phase should be from about 0.5 wt % to about 0.005 wt %, depending on the strength of the acid(s). Contact between the organic and aqueous phases in the conversion reactor 14 is preferably maintained by a mixing device disposed within reactor 14. The mixing device may be of any conventional type, such as an agitator.

The process in the conversion reactor 14 occurs in the continuous mode at a sufficient residence time of the organic phase therein to provide the dimethylbenzene alcohol conversion of above 40% and aldehyde conversion of at least 90%. The maximum preferable value of the dimethylbenzene alcohol conversion should not exceed about 99%, and the maximum preferable aldehyde conversion is about 98% to about 99.5%.

An effluent 30 from the conversion reactor 14 is forwarded to a phase separator 32. An aqueous phase 34 containing hydrogen peroxide is recycled from the phase separator 32 bottom to the conversion reactor 14. An organic phase 36 is directed to an evaporator 38 operated under vacuum for the evaporation of hydrogen peroxide and water therefrom. Concentration of a hydrogen peroxide stream 40 leaving the evaporator 38 occurs in the fractionation column 28 where the reaction water formed from reactions [1] and

[2] in the conversion reactor 14 is removed from the fractionation column 28 as an overhead stream 42.

If the optional CHP concentration stage 12 was used after stage 2, then technical cumene hydroperoxide stream 44 from the evaporator 38 is delivered to a conventional acidic cumene hydroperoxide cleavage stage 50 to produce phenol and acetone. If the optional stage 12 was not used then stream 44 will contain oxidized organic products that must be concentrated into technical CHP at an optional CHP concentration stage 62 before proceeding to the CHP cleavage stage 50. In either case, advantageously, the stream 44 contains less than 0.2 wt % dimethylbenzene alcohol. As a result, the subsequent fractionation stage is greatly simplified due to relative absence of alpha-methylstyrene and other undesirable products resulting from presence of dimethylbenzene alcohol in technical CHP prior to fractionation.

An acid catalyst stream 52 is delivered to the CHP cleavage stage 50 to accelerate the cleavage reaction. The acid stream 52 may be for example sulfuric acid. The effluent 54 from the cleavage stage 50 is then delivered to a conventional neutralization stage 56 where the acidic catalysts present in the cleavage products are neutralized. From the neutralization stage 56, a stream 58 delivers phenol, acetone and the various by-products (such as dimethylbenzene alcohol in a quantity of less than approximately 0.2 wt %), to a fractionation stage 60 for distillation of the cleavage products.

Figure 2:
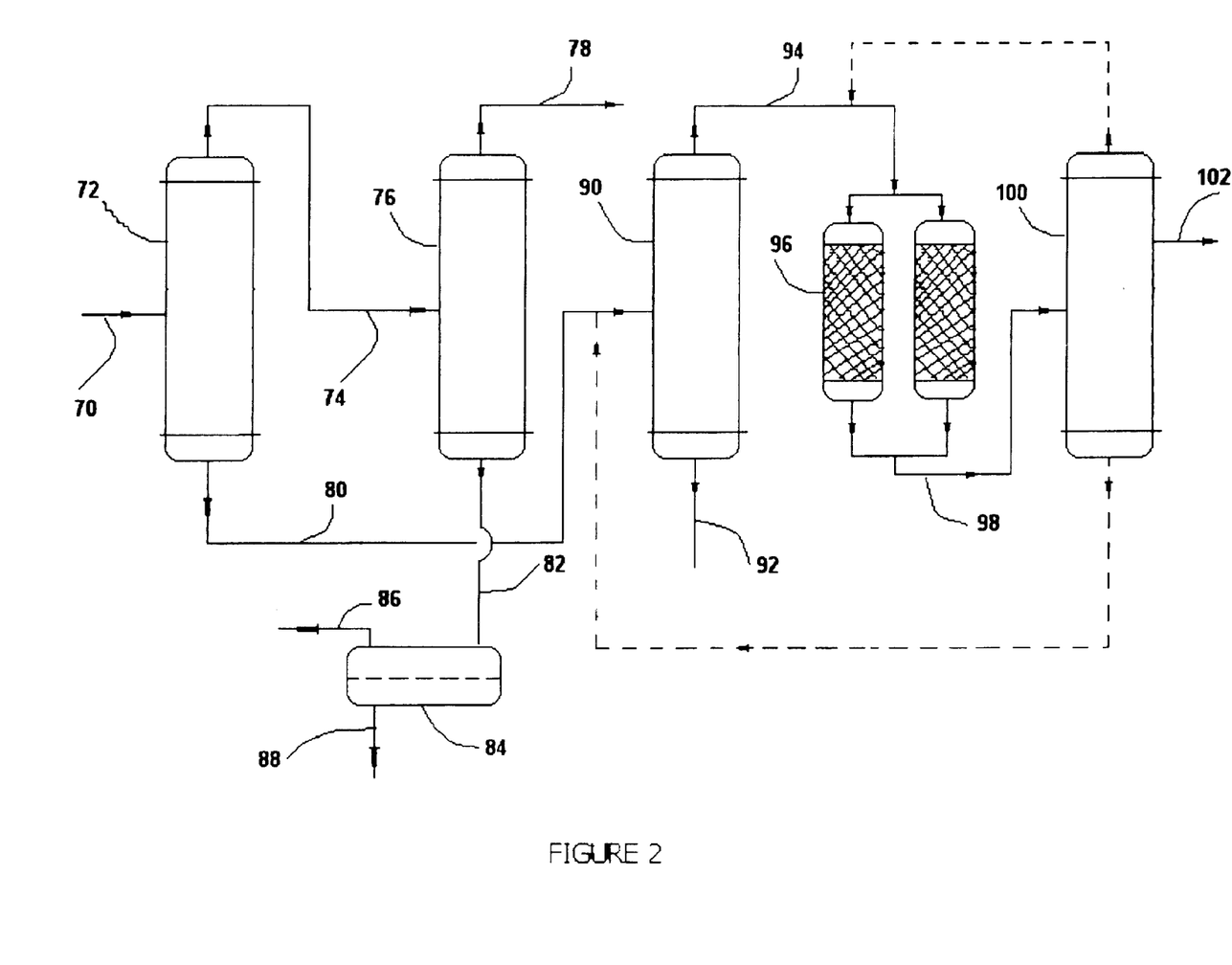
FIG. 2 schematically represents the stage of product fractionation of the inventive process of FIG. 1.

Referring now to FIG. 2, the cleavage product fractionation stage 60 is shown in greater detail. The relative absence of aldehydes and by-products such as alpha-methylstyrene, alpha-methylstyrene dimers, o-, p- phenols, and deep condensation products in the improved process developed, enables a significant simplification of the cleavage product fractionation scheme as compared to the conventional process.

As opposed to the conventional scheme, an acetone stream 74 from a top of an acetone and phenol fractionation column 72 flows directly to an acetone product column 76. The absence of aldehydes allows elimination of alkali addition to the acetone product column 76 and avoids formation of diacetone alcohol that deteriorates the desirable consumer properties of the acetone product. An acetone product stream 78 is taken overhead from the acetone product column 76.

A stream 82 is taken off the bottom of the acetone product column 76 and delivered to a phase separator vessel 84 where the aqueous phase exits at the bottom via a stream 88. Because the alpha-methylstyrene content in the cumene and by-products at the top of the vessel 84 is extremely low (less than 0.5 wt % of alpha-methylstyrene), the cumene and by-products traces are directly returned back to the cumene oxidation stage 2 via a stream 86 connecting to the stream 8. Therefore, power-intensive stages of the conventional process such as alpha-methylstyrene hydrogenation or final alpha-methylstyrene production are advantageously eliminated from the inventive process.

A phenol stream 80 from the bottom of the fractionation column 72 is forwarded to a phenol column 90 for the fractionation of heavy products in a manner similar to a conventional scheme. In absence of dimethylbenzene alcohol, there is substantially no formation of alpha-methylstyrene dimers and cumyl phenols at the cumene hydroperoxide cleavage stage 52 and, therefore, the phenol column 90 bottom product mostly comprises phenol and acetophenone. The phenol content of the phenol column 90 bottom stream 92 is about 10 wt %. Stream 92 is delivered to a phenol reclaiming stage where phenol is separated from acetophenone and by-products (not shown).

The absence of alpha-methylstyrene dimers and cumyl phenols in the phenol column 90 bottom stream 92 renders the heavy end cracking stage completely unnecessary. The phenol column 90 overhead stream 94 comprises crude phenol containing traces of alpha-methylstyrene, cumene, hydroxyacetone, and of mesityl oxide. To remove these small impurities, the phenol column 90 overhead stream 94 is sent to a catalytic treatment stage 96, wherein sulfonic ion exchange resin or zeolite is used as a catalyst, followed by delivery of products of stage 96 to a phenol finishing column 100 via a stream 98. Product phenol is taken off the phenol finishing column 100 as a side stream 102. The absence of alpha-methylstyrene in the fractionation column 72 bottom stream 80 allows for complete elimination of a water extractive distillation column that is employed in the conventional scheme, or, in existing processes, a significant reduction of the extracting agent consumption and the reflux ratio in such a column. As the extractive distillation column requires significant steam rate, the overall steam usage, therefore, decreases at the fractionation stage of the improved process.

In order to illustrate the advantages of the inventive process, presented below in form of experimental examples are the results of the oxidation of the cumene hydroperoxide phase containing dimethylbenzene alcohol and aldehydes by hydrogen peroxide, as well as the results of the cumene hydroperoxide cleavage and the fractionation of the cumene hydroperoxide cleavage products pre-treated by hydrogen peroxide products in the conversion reactor 14, in accordance with the present invention. A process disclosed in the U.S. Pat. No. 6,057,483, which currently provides the best selectivity among previously known process models, is referred to as a prototype for comparison to the final results of the inventive process. It should be noted that all numerical values, ratios, and specific utilized solutions are used by way of example only to illustrate the performance of the inventive process in a variety of experimental applications and shall not serve to limit the selection of such values for the inventive process other than as indicated in the claims appended hereto.

EXAMPLE 1

Oxidation products of the composition shown in Table 1 below were continuously introduced to the conversion reactor 14, to which a circulating aqueous hydrogen peroxide solution was also added (as described in connection with FIG. 1 above). To maintain the specified hydrogen peroxide concentration in the reactor of 33 wt %, a fresh hydrogen peroxide solution containing 35 wt % of the latter was also added to said circulating solution. The aqueous to organic phase volumetric ratio was maintained at 1:1. The temperature in the reactor was adjusted to 60° C. The contacting time was one hour. There were no acidic catalysts added to the reactor. After being treated in the reactor with aqueous hydrogen peroxide solution, the oxidation products were then forwarded to a phase separator. The separated organic phase was sent to the evaporator and analyzed. The aqueous phase recycled back to the reactor. Table 1 represents the oxidation product composition after the aldehyde/dimethylbenzene alcohol conversion reactor 14.

EXAMPLE 2

The inventive conversion oxidation process was carried out in a similar manner as in Example 1; with the difference that 0.2 wt % orthophosphoric acid was added to the circulating aqueous hydrogen peroxide solution to the reactor. The results obtained are shown in Table 1 .

EXAMPLE 3

The inventive conversion oxidation process was carried out in a similar manner as in Example 1; with the difference that 10 wt % acetic acid was added to the circulating aqueous hydrogen peroxide solution to the reactor 14. As the acetic acid solubility in the organic phase was about 1.4 wt % under the process conditions, a fresh acetic acid solution was added to the reactor 14 to keep the acetic acid concentration constant. The results obtained are shown in Table 1.

EXAMPLE 4

The inventive conversion oxidation process was carried out in a similar manner as in Example 1; with the difference that 0.0060 wt % sulfuric acid was added to the circulating aqueous hydrogen peroxide solution to the reactor. The results obtained are shown in Table 1.

TABLE 1

(Examples 1–4)

Oxidation product composition, wt%

| Components | At the conversion reactor 14 inlet | At the conversion reactor 14 outlet ||||
|---|---|---|---|---|---|
| | | Example 1 | Example 2 | Example 3 | Example 4 |
| Dimethylbenzene alcohol | 1.26 | 1.10 | 0.40 | 0.70 | 0.02 |
| Dicumyl peroxide | 0.05 | 0.05 | 0.05 | 0.05 | 0.05 |
| Acetophenone | 0.16 | 0.16 | 0.16 | 0.16 | 0.16 |
| Cumene hydroperoxide | 24.78 | 24.98 | 25.82 | 25.46 | 26.28 |
| Cumene | 73.70 | 73.71 | 73.57 | 73.63 | 73.49 |
| Aldehydes | 0.05 | None | None | None | None |
| Dimethylbenzene alcohol conversion, % | | 12.7 | 68.3 | 44.4 | 98.4 |
| Aldehydes conversion, % | | 100 | 100 | 100 | 100 |
| Selectivity, % mole | | 93.70 | 94.38 | 97.34 | 96.08 | 98.94 |

EXAMPLE 5

The inventive conversion oxidation process was carried out in a similar manner as in Example 2; with the difference that technical cumene hydroperoxide of a various content of cumene and dimethylbenzene alcohol was fed to the reactor 14, and the hydrogen peroxide concentration of the aqueous phase was maintained at 50 wt %. The results obtained are shown in Table 2. Furthermore, 0.05 wt % aqueous orthophosphoric acid was added to stabilize the aqueous hydrogen peroxide solution.

TABLE 2

(Example 5)

Oxidation product composition, wt %

| Components | CR inlet | CR outlet | CR inlet | CR outlet | CR inlet | CR outlet | CR inlet | CR outlet |
|---|---|---|---|---|---|---|---|---|
| Dimethylbenzene alcohol | 7.83 | 0.89 | 3.85 | 0.44 | 3.35 | 0.25 | 3.50 | 0.40 |
| Dicumyl peroxide | 0.85 | 0.84 | 0.276 | 0.275 | 0.21 | 0.21 | 0.20 | 0.20 |
| Acetophenone | 1.44 | 1.43 | 0.53 | 0.53 | 0.40 | 0.40 | 0.60 | 0.60 |
| Cumene hydroperoxide | 88.50 | 95.47 | 83.514 | 86.976 | 66.04 | 69.25 | 94.60 | 97.80 |
| Cumene | 1.28 | 1.37 | 11.83 | 11.78 | 30.00 | 29.89 | 1.00 | 1.00 |
| Aldehydes | 0.10 | 0.01 | 0.05 | 0.005 | 0.05 | 0.005 | 0.10 | 0.01 |
| Dimethylbenzene alcohol conversion, % | | 88.6 | | 88.6 | | 92.5 | | 88.6 |
| Aldehydes conversion, % | | 99 | | 99 | | 99 | | 99 |
| Selectivity, % mole | 88.47 | 96.22 | 94.05 | 98.33 | 93.64 | 98.54 | 95.08 | 98.56 |

CR = conversion reactor 14

EXAMPLE 6

The inventive conversion oxidation process was carried out in a similar manner as in Example 2; with the difference that the aqueous to organic volumetric ratio was maintained at 4:1. For a 0.5 hour contacting period, the dimethylbenzene alcohol conversion was 90%. The results obtained are shown in Table 3.

EXAMPLE 7

The inventive conversion oxidation process was carried out in a similar manner as in Example 2; with the difference that the hydrogen peroxide concentration in the aqueous phase in the reactor 14 was 53 wt %. For 0.38 hour contacting period, the dimethylbenzene alcohol conversion was 90%. The results obtained are shown in Table 3.

EXAMPLE 8

The inventive conversion oxidation process was carried in a similar manner as in Example 7; with the difference that the temperature was adjusted in the reactor 14 to be 70° C. For 0.16 hour contacting period, the dimethylbenzene alcohol conversion was 90%. The results obtained are shown in Table 3.

TABLE 3

(Examples 6–8)

| Components | CR inlet | CR outlet Examples 6–8 |
|---|---|---|
| | | Oxidation product composition, wt % |
| Dimethylbenzene alcohol | 1.26 | 0.11 |
| Dicumyl peroxide | 0.05 | 0.05 |
| Acetophenone | 0.16 | 0.16 |
| Cumene hydroperoxide | 24.78 | 26.17 |
| Cumene | 73.70 | 73.51 |
| Aldehydes | 0.05 | None |
| Dimethylbenzene alcohol conversion, % | | 90.0 |
| Aldehydes conversion, % | | 100 |
| Selectivity, % mole | 93.70 | 98.57 |

EXAMPLE 9

The inventive conversion oxidation process was carried out in a similar manner as in Example 8; with the difference that the intermediate fractionation column bottoms having a technical cumene hydroperoxide concentration of 50 wt % was fed to the reactor 14, maintaining the aqueous to organic phase volumetric ratio at 4:1. For 0.06 hour contacting period, the dimethylbenzene alcohol conversion was 98%. The results obtained are shown in Table 4.

TABLE 4

| Components | CR inlet | CR outlet Example 9 |
|---|---|---|
| | | Oxidation product composition, wt % |
| Dimethylbenzene alcohol | 2.54 | 0.08 |
| Dicumyl peroxide | 0.10 | 0.11 |
| Acetophenone | 0.32 | 0.34 |
| Cumene hydroperoxide | 50.00 | 53.12 |
| Cumene | 46.99 | 46.35 |
| Aldehydes | 0.05 | None |
| Dimethylbenzene alcohol conversion, % | | 98.1 |
| Aldehydes conversion, % | | 100 |
| Selectivity, % mole | 93.70 | 98.81 |

EXAMPLE 10

The experiment of Example 10 demonstrates the properties of acetone product in the improved process. Technical cumene hydroperoxide having the compositions shown in Table 5 below produced by both the conventional process and the improved process respectively, was directed to the acidic cumene hydroperoxide cleavage stage to produce phenol and acetone and further to the neutralization stage.

TABLE 5

(Example 10)

| Process | Dimethyl benzene alcohol | Dicumyl peroxide | Acetophenone | Cumene hydroperoxide | Cumene | Selectivity mole % |
|---|---|---|---|---|---|---|
| Conventional | 4.22 | 0.17 | 0.53 | 82.99 | 12.09 | 93.7 |
| Improved | 0.07 | 0.17 | 0.52 | 87.27 | 11.97 | 98.9 |

The neutralized cleavage products obtained at the conventional process were forwarded to the acetone production stage according to the conventional scheme. The cleavage products from the improved process were forwarded to the fractionation stage, as shown in FIG. 2. Table 6 compares the properties of the acetone product in the improved process vs. the conventional process.

TABLE 6

(Example 10)

| Components | Conventional Process | Improved Process |
|---|---|---|
| | Composition, ppm | |
| Acetaldehyde | 15 | None |
| Propionic aldehyde | 5 | None |
| Crotonic aldehyde | 5 | None |
| Mesityl oxide | 5 | 2 |
| Diacetone alcohol | 30 | 2 |
| Acetic acid | 12 | 2 |
| KT, hr | 4 | 12 |

EXAMPLE 11

The experiment of Example 11 demonstrates the overall improved process efficiency based on an increased phenol production rate. Basis: 50,000 kg/hr of technical cumene hydroperoxide having the composition shown in Table 7 are produced at the oxidation stage and the conversion reactor 14. Technical cumene hydroperoxide produced at the conventional process and the improved process respectively, were forwarded to the acidic cumene hydroperoxide cleavage stage to produce phenol and acetone. The composition of the cleavage products obtained is shown in Table 7. The conventional cleavage process of U.S. Pat. No. 6,057,483 was used at the cleavage stage.

TABLE 7

(Experiment 11)

| Components | Conventional Process | Improved Process |
|---|---|---|
| | Composition, wt % | |
| Dimethylbenzene alcohol | 0.115 | 0.01 |
| Dicumyl peroxide | 0.06 | 0.06 |
| Alpha-methylstyrene | 3.333 | 0.094 |
| Cumyl phenols | 0.199 | 0.004 |
| Alpha-methylstyrene dimers | 0.134 | 0.003 |
| Cumene | 11.987 | 11.798 |
| Acetophenone | 0.525 | 0.513 |
| Phenol | 50.83 | 53.23 |
| Acetone | 31.42 | 32.84 |
| Alpha-methylstyrene yield, % | 90.0 | |
| Total heavy components, wt. % | 1.033 | 0.59 |

Note: Total heavy components comprise dimethylbenzene alcohol, dicumyl peroxide, alpha-methylstyrene dimers, cumyl phenols, and acetophenone.

The cleavage products obtained by improved methods were sent to the subsequent stage of neutralization and cleavage products fractionation. The observed increase of the overall phenol and acetone production and reduction of the phenol tars formation both at the cleavage stage and the fractionation stage are shown in Table 8 below. The cumene consumption coefficient, based on the improved process with the capacity expansion, was 1291 kg/hr, which is 19 kg/t lower compared to the conventional process.

TABLE 8

(Example 11)

| Process | Phenol, kg/hr | Acetone, kg/hr | Tars, kg/t phenol | Losses at the fractionation stage, kg/t phenol | Total phenol tars, kg/t phenol | Cumene consumption coefficient, kg/t phenol |
|---|---|---|---|---|---|---|
| Conventional | 25634 | 15848 | 20 | 15.4 | 35.4 | 1310 |
| Improved | 27001 | 16664 | 12 | 3.88 | 15.88 | 1291 |
| Delta | +1367 | +816 | −8 | −11.52 | −19.52 | −19 |

EXAMPLE 12

The experiment of Example 12 demonstrates the improved process efficiency at the same phenol production rate. At the same phenol production rate, the oxidation stage of the inventive process will operate under lower temperatures as compared to the conventional process, which leads to further reduction of the acetophenone and dicumyl peroxide concentration in technical cumene hydroperoxide. In this case, the technical cumene hydroperoxide feed-rate to cleavage stage will be 47,845 kg/hr, and the composition as shown in Table 9.

TABLE 9

(Experiment 12)

| Process | Dimethyl benzene alcohol | Dicumyl peroxide | Acetophenone | Cumene hydroperoxide | Cumene | Selectivity, % mole |
|---|---|---|---|---|---|---|
| Conventional | 4.22 | 0.17 | 0.53 | 82.99 | 12.09 | 93.6 |
| Improved | 0.07 | 0.1 | 0.46 | 87.28 | 12.09 | 99.1 |

Technical cumene hydroperoxide produced by both conventional process and improved process respectively, was forwarded to the acidic cumene hydroperoxide cleavage stage to produce phenol and acetone. The composition of the cleavage products obtained is shown in Table 10. The conventional cleavage process of U.S. Pat. No. 6,057,483 was used at the cleavage stage.

TABLE 10

(Experiment 12)

| Components | Composition, wt % | |
|---|---|---|
| | Conventional Process | Improved Process |
| Dimethylbenzene alcohol | 0.115 | 0.009 |
| Dicumyl peroxide | 0.06 | 0.059 |
| Alpha-methylstyrene | 3.333 | 0.066 |
| Cumyl phenols | 0.199 | 0.003 |
| Alpha-methylstyrene dimers | 0.134 | 0.002 |
| Cumene | 11.987 | 11.918 |
| Acetophenone | 0.525 | 0.453 |
| Phenol | 50.53 | 53.22 |
| Acetone | 31.42 | 32.84 |
| Alpha-methylstyrene yield, % | 90.0 | |
| Total heavies, wt. % | 1.033 | 0.526 |

The cleavage products were then sent to the subsequent stage of neutralization and cleavage products fractionation. Improved operating conditions of the oxidation stage led to the reduction of the phenol tar formation both at the cleavage stage and the fractionation stage, as shown in Table 11. The cumene consumption coefficient, based on the improved process under the constant capacity, is 1287 kg/hr, which is 23 kg/t lower as compared to the conventional process.

TABLE 11

(Experiment 12)

| Process | Phenol, kg/hr | Acetone, kg/hr | Tars, kg/t phenol | Losses at the fractionation stage, kg/t phenol | Total phenol tars, kg/t phenol | Cumene consumption coefficient, kg/t phenol |
|---|---|---|---|---|---|---|
| Conventional | 25634 | 15848 | 20 | 15.4 | 35.4 | 1310 |
| Improved | 25634 | 15848 | 8 | 2.6 | 10.6 | 1287 |
| Delta | | | −12 | −12.8 | −24.8 | −23 |

The terms, examples, and expressions that have been employed in this disclosure are used as terms of description and not of limitation. The terms, examples, and expressions are intended to illustrate the key features of this invention. The exclusion of such terms and expressions can be recognized as modifications and are within the scope of the invention.

Thus, while there have shown and described and pointed out fundamental novel features of the invention as applied to preferred embodiments thereof, it will be understood that various omissions and substitutions and changes in the form and details of the process schemes and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method for increasing selectivity and productivity of a cumene process of phenol and acetone production comprising the steps of:
    (a) treating, in a conversion reactor, organic cumene oxidation products containing from about 16 wt% to about 94 wt% cumene hydroperoxide, cumene, and by-products comprising at least dimethylbenzene alcohol and aldehydes, with the use of a hydrogen peroxide in a mutually insoluble organic and aqueous phase system of an aqueous hydrogen peroxide solution and an organic solution of said cumene oxidation products; and
    (b) mixing said organic phase cumene oxidation products with the aqueous phase hydrogen peroxide solution by use of a mixing device disposed within said conversion reactor, at a temperature of about 40° C. to about 75° C., such that dimethylbenzene alcohol and said aldehydes are subject to a heterophase oxidation reaction with hydrogen peroxide so that dimethylbenzene alcohol is oxidized into cumene hydroperoxide and said aldehydes are oxidized into corresponding organic acids.

2. The method of claim 1, wherein hydrogen peroxide concentration in said aqueous solution of hydrogen peroxide is selected from a range of: from about 1% to about 70%, further comprising the step of:

(c) maintaining said selected hydrogen peroxide concentration at a substantially stable value.

3. The method of claim 2, wherein said step (c) comprises the step of:

(d) adding additional hydrogen peroxide aqueous solution into said conversion reactor, said additional hydrogen peroxide aqueous solution having a sufficient hydrogen peroxide concentration sufficient to maintain said selected hydrogen peroxide concentration in said conversion reactor.

4. The method of claim 2, wherein said step (c) further comprises the step of:

(e) feeding a hydrogen peroxide stabilizing agent into said conversion reactor to maintain said selected hydrogen peroxide concentration in said conversion reactor.

5. The method of claim 1, further comprising the step of:

(f) feeding an acidic catalyst into said conversion reactor to accelerate said oxidation reaction at said step (b).

6. The method of claim 5, wherein said acidic catalyst comprises at least one acid selected from the following groups of acids:

1) weak organic acids, and
2) acids of average strength.

7. The method of claim 2, wherein said step (c) comprises the step of:

(g) adding a stabilizing catalytic agent to said conversion reactor to maintain said elected hydrogen peroxide concentration at a substantially stable value, and to provide an acidic catalyst for said oxidation reaction.

8. The method of claim 7, wherein said stabilizing catalytic agent is aqueous phosphoric acid.

9. The method of claim 8, wherein said aqueous phosphoric acid is maintained at a concentration from about 0.1 wt% to about 0.5 wt% of said aqueous hydrogen peroxide phase.

10. The method of claim 1, further comprising the step of:

(h) maintaining the weight ratio of said aqueous and organic phases in said conversion reactor within the range of about 0.1:1 to about 10:1.

11. The method of claim 1, further comprising the step of:

(i) separating said oxidized organic products in said organic phase after contacting with hydrogen peroxide from said aqueous hydrogen peroxide phase at a phase separation stage, wherein said oxidized organic products contain less than 0.2 wt % of dimethylbenzene alcohol.

12. The method of claim 11, further comprising the step of:

(j) delivering said oxidized organic products to an evaporator to evaporate hydrogen peroxide therefrom under vacuum.

13. The method of claim 12, further comprising the steps of:

(k) concentrating said evaporated hydrogen peroxide in a fractionation column to produce water and aqueous hydrogen peroxide;
(l) recycling said aqueous hydrogen peroxide to said conversion reactor, and
(m) removing water from said fractionation column.

14. The method of claim 12, further comprising the step of:

(n) concentrating said oxidized organic products in a cumene hydroperoxide concentration stage to produce technical cumene hydroperoxide and by-products.

15. The method of claim 14, further comprising the steps of:

(o) directing said technical cumene hydroperoxide and by-products to a cumene hydroperoxide cleavage stage to produce output products containing at least phenol and acetone;
(p) adding an acidic catalyst to said cumene hydroperoxide cleavage stage to accelerate said step (o) cleavage process; and
(q) directing said output products to a neutralization stage to neutralize said acidic catalyst added at said step (p).

16. The method of claim 15, further comprising the step of:

(r) directing said neutralized output products, from said step (q) to a cumene hydroperoxide cleavage products fractionation stage to extract product phenol and acetone therefrom.

17. The method of claim 16, wherein said step (r) further comprises the steps of:

(s) directing said neutralized output products from said step (q) to an acetone and phenol fractionation column having a top and a bottom; and
(t) delivering an acetone stream from said top of said acetone and phenol fractionation column to an acetone product column to extract final product acetone from a top of said acetone product column.

18. The method of claim 17, further comprising the steps of:

(u) delivering an acetone by-product stream from a bottom of said acetone product column to a phase separator vessel to separate cumene and by-products from an aqueous phase in said acetone by-product stream;
(v) removing said aqueous phase from a bottom of said phase separator vessel; and
(w) removing said cumene and said by-products from a top of said phase separator vessel.

19. The method of claim 18, further comprising the steps of:

(x) prior to said step (a), oxidizing cumene with air oxygen in an oxidation reactor to produce organic cumene oxidation products containing from about 16 wt % to about 45 wt % cumene hydroperoxide, cumene, and by-products comprising at least dimethylbenzene alcohol and aldehydes; and
(y) delivering said cumene and by-products from said step (w) to said oxidation reactor.

20. The method of claim 19, further comprising the step of:

(z) after said step (y) and before said step (a), concentrating said organic cumene oxidation products in a concentration stage to produce organic cumene oxidation products containing from about 60 wt % to about 94 wt % cumene hydroperoxide and by-products comprising at least dimethylbenzene alcohol and aldehydes.

21. The method of claim 17, further comprising the steps of:

(aa) delivering a phenol stream from said bottom of said acetone and phenol fractionation column to a phenol column to perform fractionation of heavy products; and
(bb) removing a bottom product containing at least phenol and acetophenone from a bottom of said phenol column to a phenol reclaiming stage.

22. The method of claim 21, further comprising the steps of:

(cc) delivering a crude phenol and trace by-products stream from a top of said phenol column to a catalytic treatment stage to produce treated phenol;

(dd) delivering said treated phenol to a phenol finishing column to extract final product phenol therefrom; and (ee) removing said final product phenol from a side of said phenol finishing column.

23. The method of claim 11, further comprising the steps of:

(ff) recycling said separated unconverted hydrogen peroxide from said aqueous hydrogen peroxide phase to said conversion reactor.

24. The method of claim 1, wherein said aldehydes comprise at least: aliphatic $C_1$–$C_3$ aldehydes, and benzoic aldehyde, and wherein said cumene oxidation products further comprise acetophenone and dicumylperoxide.

25. A method for increasing selectivity and productivity of a cumene process of phenol and acetone production comprising the steps of:

(a) treating, in a conversion reactor, organic cumene oxidation products containing from about 16 wt % to about 94 wt % cumene hydroperoxide, cumene, and by-products comprising at least dimethylbenzene alcohol and aldehydes, with the use of a hydrogen peroxide in a mutually insoluble organic and aqueous phase system of an aqueous hydrogen peroxide solution and an organic solution of said cumene oxidation products;

(b) maintaining hydrogen peroxide concentration at a substantially stable value selected from a range of about 20 wt % to about 50 wt %; and (c) mixing said organic phase cumene oxidation products with the aqueous phase hydrogen peroxide solution by use of a mixing device disposed within said conversion reactor, at a temperature of about 40° C. to about 75° C., such that dimethylbenzene alcohol and said aldehydes are subject to a heterophase oxidation reaction with hydrogen peroxide so that dimethylbenzene alcohol is oxidized into cumene hydroperoxide and said aldehydes are oxidized into corresponding organic acids.

26. The method of claim 25, further comprising the step of:

(d) maintaining the weight ratio of said aqueous and organic phases in said conversion reactor within the range of about 1:1 to about 6:1.

27. A method for increasing selectivity and productivity of a cumene process of phenol and acetone production comprising the steps of:

(a) oxidizing cumene with air oxygen in an oxidation reactor to produce organic cumene oxidation products containing from about 16 wt % to about 45 wt % cumene hydroperoxide, cumene, and by-products comprising at least dimethylbenzene alcohol and aldehydes, (b) concentrating said organic cumene oxidation products in a concentration stage to produce concentrated organic cumene oxidation products containing from about 60 wt % to about 94 wt % cumene hydroperoxide and by-products comprising at least dimethylbenzene alcohol and aldehydes;

(c) treating said concentrated organic cumene oxidation products in a conversion reactor, with the use of a hydrogen peroxide in a mutually insoluble organic and aqueous phase system of an aqueous hydrogen peroxide solution and an organic solution of said concentrated cumene oxidation products; and (d) mixing said organic phase concentrated cumene oxidation products with the aqueous phase hydrogen peroxide solution by use of a mixing device disposed within said conversion reactor, at a temperature of about 40° C. to about 75° C., such that dimethylbenzene alcohol and said aldehydes are subject to a heterophase oxidation reaction with hydrogen peroxide so that dimethylbenzene alcohol is oxidized into cumene hydroperoxide and said aldehydes are oxidized into corresponding organic acids.

28. The method of claim 27, wherein hydrogen peroxide concentration in said aqueous solution of hydrogen peroxide is selected from a range of: from about 20% to about 50%, further comprising the step of:

(e) maintaining said selected hydrogen peroxide concentration at a substantially stable value.

29. The method of claim 28, wherein said step (e) comprises the step of:

(f) adding additional hydrogen peroxide aqueous solution into said conversion reactor, said additional hydrogen peroxide aqueous solution having a sufficient hydrogen peroxide concentration sufficient to maintain said selected hydrogen peroxide concentration in said conversion reactor.

30. The method of claim 28, wherein said step (e) further comprises the step of:

(g) feeding a hydrogen peroxide stabilizing agent into said conversion reactor to maintain said selected hydrogen peroxide concentration in said conversion reactor.

31. The method of claim 27, further comprising the step of:

(h) feeding an acidic catalyst into said conversion reactor to accelerate said oxidation reaction at said step (c).

32. The method of claim 28, wherein said step (e) comprises the step of:

(i) adding a stabilizing catalytic agent to said conversion reactor to maintain said selected hydrogen peroxide concentration at a substantially stable value, and to provide an acidic catalyst for said oxidation reaction.

33. The method of claim 32, wherein said stabilizing catalytic agent is aqueous phosphoric acid maintained at a concentration from about 0.1 wt % to about 0.5 wt % of said aqueous hydrogen peroxide phase.

34. The method of claim 27, further comprising the step of:

(j) maintaining the weight ratio of said aqueous and organic phases in said conversion reactor within the range of about 1:1 to about 6:1.

35. The method of claim 27, further comprising the step of:

(k) separating said oxidized organic products in said organic phase after contacting with hydrogen peroxide from said aqueous hydrogen peroxide phase at a phase separation stage, wherein said oxidized organic products contain less than 0.2 wt % of dimethylbenzene alcohol.

36. The method of claim 35, further comprising the step of:

(l) delivering said oxidized organic products to an evaporator to evaporate hydrogen peroxide therefrom under vacuum, such that only technical cumene hydroperoxide and by-products remain.

37. The method of claim 36, further comprising the steps of:

(m) concentrating said evaporated hydrogen peroxide in a fractionation column to produce water and aqueous hydrogen peroxide;

(n) recycling said aqueous hydrogen peroxide to said conversion reactor; and (o) removing water from said fractionation column.

38. The method of claim 36, further comprising the steps of:
- (p) directing said technical cumene hydroperoxide and by-products to a cumene hydroperoxide cleavage stage to produce output products containing at least phenol and acetone;
- (q) adding an acidic catalyst to said cumene hydroperoxide cleavage stage to accelerate said step (p) cleavage process; and
- (r) directing said output products to a neutralization stage to neutralize said acidic catalyst added at said step (q).

39. The method of claim 38, further comprising the steps of:
- (s) directing said neutralized output products, from said step (r) to a cumene hydroperoxide cleavage products fractionation stage to extract product phenol and acetone therefrom.

40. The method of claim 35, further comprising the steps of:
- (t) recycling said separated unconverted hydrogen peroxide from said aqueous hydrogen peroxide phase to said conversion reactor.

41. The method of claim 39, wherein said step (s) further comprises the steps of:
- (u) directing said neutralized output products from said step (r) to an acetone and phenol fractionation column having a top and a bottom; and
- (v) delivering an acetone stream from said top of said acetone and phenol fractionation column to an acetone product column to extract final product acetone from a top of said acetone product column.

42. The method of claim 41, further comprising the steps of:
- (w) delivering an acetone by-product stream from a bottom of said acetone product column to a phase separator vessel to separate cumene and by-products from an aqueous phase in said acetone by-product stream;
- (x) removing said aqueous phase from a bottom of said phase separator vessel; and
- (y) removing said cumene and said by-products from a top of said phase separator vessel.

43. The method of claim 42, further comprising the step of:
- (z) delivering said cumene and by-products from said step (y) to said oxidation reactor.

44. The method of claim 41, further comprising the steps of:
- (aa) delivering a phenol stream from said bottom of said acetone and phenol fractionation column to a phenol column to perform fractionation of heavy products; and
- (bb) removing a bottom product containing at least phenol and acetophenone from a bottom of said phenol column to a phenol reclaiming stage.

45. The method of claim 44, further comprising the steps of:
- (cc) delivering a crude phenol and trace by-products stream from a top of said phenol column to a catalytic treatment stage to produce treated phenol;
- (dd) delivering said treated phenol to a phenol finishing column to extract final product phenol therefrom; and
- (ee) removing said final product phenol from a side of said phenol finishing column.

46. The method of claim 27, wherein said aldehydes comprise at least: aliphatic $C_1$–$C_3$ aldehydes, and benzoic aldehyde, and wherein said cumene oxidation products further comprise acetophenone and dicumylperoxide.

47. The method of claim 6, wherein said weak organic acid group comprises: formic acids, acetic acids, propionic acids, and benzoic acids.

48. The method of claim 6, wherein said average strength acid group comprises: fluorine, chlorine substituted acids of aliphatic range, mono-di-trichloracidicacids and mixtures thereof, mineral acids, and heterogeneous acidic catalysts.

49. The method of claim 48, wherein said mineral acids comprise: $H_3PO_4$, $H_2SO_4$, HCl, $HClO_4$, $H_2SO_3$, and $SO_2$.

50. The method of claim 48, wherein said heterogeneous acidic catalysts comprise: sulfonic ion exchange resins, naphiones, and acidic zeolites.

* * * * *